(12) United States Patent
Liu et al.

(10) Patent No.: US 12,115,390 B2
(45) Date of Patent: *Oct. 15, 2024

(54) CONTROL DRIVING METHOD FOR A RADIOTHERAPY DEVICE

(71) Applicant: OUR UNITED CORPORATION, Xi'an (CN)

(72) Inventors: Haifeng Liu, Xi'an (CN); Daliang Li, Xi'an (CN)

(73) Assignee: OUR UNITED CORPORATION (CN)

( * ) Notice: Subject to any disclaimer, the term of this patent is extended or adjusted under 35 U.S.C. 154(b) by 918 days.

This patent is subject to a terminal disclaimer.

(21) Appl. No.: 17/174,778

(22) Filed: Feb. 12, 2021

(65) Prior Publication Data
US 2021/0187325 A1 Jun. 24, 2021

Related U.S. Application Data

(63) Continuation-in-part of application No. 16/805,418, filed on Feb. 28, 2020, now Pat. No. 10,953,244, (Continued)

(30) Foreign Application Priority Data

Aug. 24, 2018 (CN) .......................... 201810975999.X

(51) Int. Cl.
A61N 5/10 (2006.01)
(52) U.S. Cl.
CPC ......... *A61N 5/1065* (2013.01); *A61N 5/1042* (2013.01); *A61N 5/1049* (2013.01);
(Continued)

(58) Field of Classification Search
CPC .. A61N 5/1065; A61N 5/1042; A61N 5/1049; A61N 5/1081; A61N 5/1084;
(Continued)

(56) References Cited

U.S. PATENT DOCUMENTS

| 6,044,126 A | 3/2000 | Rousseau et al. |
| 2009/0086909 A1 | 4/2009 | Hui et al. |
| 2017/0065834 A1* | 3/2017 | Liu ...................... A61N 5/1047 |

FOREIGN PATENT DOCUMENTS

| CN | 101195058 | 6/2008 |
| CN | 101195058 A * | 6/2008 |

(Continued)

*Primary Examiner* — Thaddeus B Cox
*Assistant Examiner* — Joshua Daryl D Lannu
(74) *Attorney, Agent, or Firm* — Emerson, Thomson & Bennett, LLC; Roger D. Emerson; Matt J. Wilson

(57) ABSTRACT

A control driving method for a radiotherapy device is disclosed. The radiotherapy device includes a collimator and a plurality of radioactive sources, wherein the radioactive sources are disposed within a preset angle range in a longitude direction, the longitude direction being a circular direction perpendicular to a central axis of the radiotherapy device, and the radioactive sources are configured to emit beams that intersect at a common focus after being collimated by a collimator. The method comprises: obtaining at least one protection angle range and driving the radiotherapy device such that no beam from the plurality of the radioactive sources within the at least one protection angle range is emitted.

18 Claims, 13 Drawing Sheets

Related U.S. Application Data which is a continuation of application No. PCT/CN2019/099390, filed on Aug. 6, 2019.

(52) U.S. Cl.
CPC ......... *A61N 5/1081* (2013.01); *A61N 5/1084* (2013.01); *A61N 2005/1052* (2013.01); *A61N 2005/1055* (2013.01); *A61N 2005/1061* (2013.01); *A61N 2005/1062* (2013.01); *A61N 2005/1074* (2013.01); *A61N 2005/1094* (2013.01)

(58) Field of Classification Search
CPC .... A61N 2005/1052; A61N 2005/1055; A61N 2005/1061; A61N 2005/1062; A61N 2005/1074; A61N 2005/109
See application file for complete search history.

(56) References Cited

FOREIGN PATENT DOCUMENTS

| | | | |
|---|---|---|---|
| EP | 1057499 A2 | 12/2000 | |
| JP | S63024200 A | 2/1988 | |
| JP | H05200126 A | 8/1993 | |
| JP | 2017504449 | 2/2017 | |
| JP | 2018508277 A | 3/2018 | |
| JP | 2018522651 A | 8/2018 | |
| WO | WO1996/031253 A1 | 4/1996 | |
| WO | 2017020244 | 2/2017 | |
| WO | WO-2017020244 A1 * | 2/2017 | ............... A61N 5/01 |

* cited by examiner

CONTROL DRIVING METHOD FOR A RADIOTHERAPY DEVICE

CROSS REFERENCE TO RELATED APPLICATIONS

The present disclosure is a continuation-in-part of U.S. application Ser. No. 16/805,418 filed on Feb. 28, 2020 and entitled "CONTROL DRIVING METHOD FOR RADIOTHERAPY DEVICE", which is a continuation of international application No. PCT/CN2019/099390 filed on Aug. 6, 2019, which claims priority to the Chinese application No. 201810975999.X filed on Aug. 24, 2018, the contents of which are hereby incorporated by reference in its entireties.

TECHNICAL FIELD

The present disclosure relates to the field of medical technologies, and more particularly, to a source body, a radiotherapy device, and a control driving method thereof.

BACKGROUND

With the development of medical technologies, radiation treatment is more and more widely used in the treatment of tumors.

In related technologies, a radiotherapy device used for treating heads mainly includes a head gamma knife. Actually, a natural isotope radioactive source, cobalt-60, is utilized to emit gamma rays, and radioactivity of the rays is utilized to kill tumor cells. However, the rays may also damage normal tissues or cells. In the related technologies, the head gamma knife includes 30 or 180 radioactive sources, and a plurality of radioactive sources emit beams from different directions and focus on a common focus, such that the common focus has the largest gamma-ray dose rate, whereas the beams emitted from each radioactive source cause less damage to the normal tissues or cells. In this way, an objective of killing the tumor cells while protecting the normal tissues or cells is achieved, thereby achieving tumor treatment effects.

SUMMARY

The present disclosure provides a source body, a radiotherapy device, and a control driving method thereof. The technical solutions are described as follows.

In one aspect, the present disclosure provides a source body. The source body is provided with a plurality of radioactive sources, and an included angle between the plurality of radioactive sources in a longitudinal direction are within a preset included angle range.

In another aspect, the present disclosure provides a radiotherapy device. The radiotherapy device includes a radioactive source apparatus. The radioactive source apparatus includes a source body and a collimator provided by the present disclosure. Beams emitted from the plurality of radioactive sources on the source body intersect at a common focus after being collimated by the collimator.

In still another aspect, the present disclosure provides a control driving method for a radiotherapy device. The radiotherapy device is the radiotherapy device according to any embodiment of the present disclosure. The method includes: obtaining at least one beam emission angle range; and driving the radiotherapy device to emit beams within the beam emission angle range and to ensure the beams to intersect at a common focus.

BRIEF DESCRIPTION OF THE DRAWINGS

To describe the technical solutions of the embodiments of the utility model more clearly, the accompanying drawings required for describing the embodiments will be briefly introduced below. Apparently, the accompanying drawings in the following description are merely some embodiments of the present disclosure. To those of ordinary skills in the art, other accompanying drawings may also be derived from these accompanying drawings without creative efforts.

DETAILED DESCRIPTION OF THE EMBODIMENTS

Detailed description of implementations of the present disclosure will further be made with reference to drawings in order to make the above objects, technical solutions and advantages of the present disclosure more apparent.

Figure 1:
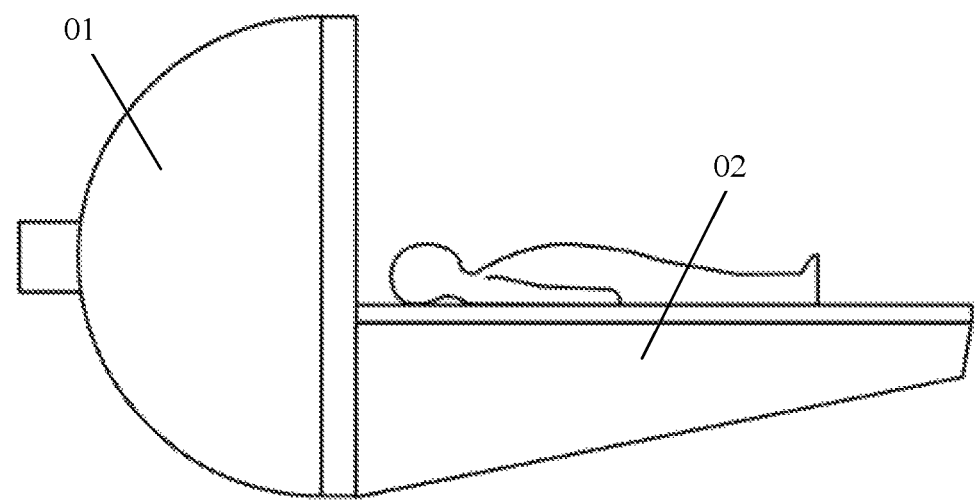
FIG. 1 is a schematic structural diagram of a radiotherapy device in related technologies according to an embodiment of the present disclosure.
Figure 2:
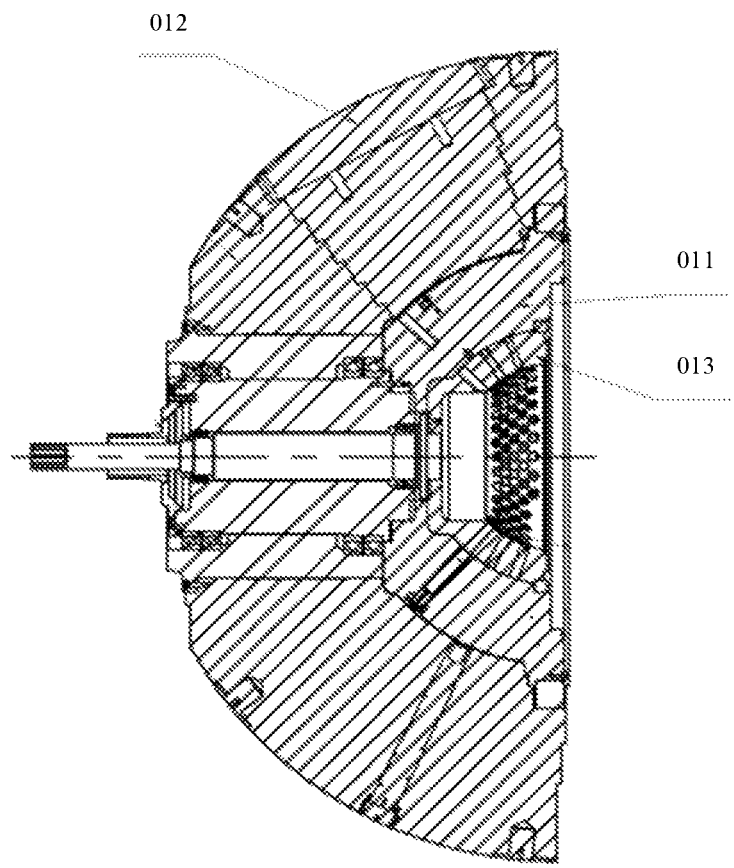
FIG. 2 is a schematic structural diagram of a radioactive source apparatus in related technologies according to an embodiment of the present disclosure.

In related technologies, a radiotherapy device used for treating head tumors has a structure for radiation treatment of the head tumors as shown in FIG. 1 and FIG. 2. The radiotherapy device may include a radioactive source apparatus 01 and a treatment couch 02. The radioactive source apparatus 01 may include a source body 011, a shield body 012, and a collimator 013. A plurality of radioactive source (not marked in FIG. 2) may be mounted in the source body 011. Beams emitted from the plurality of radioactive sources intersect at a common focus after passing through a collimation hole (not marked in FIG. 2) on the collimator 02, and the common focus is located in a cavity of the radioactive source apparatus 01. The treatment couch 02 is used to carry a patient and to move the patient into a treatment cabin of the radioactive source apparatus 01, such that a nidus of the patient is located at the common focus for radiation treatment.

Figure 3:
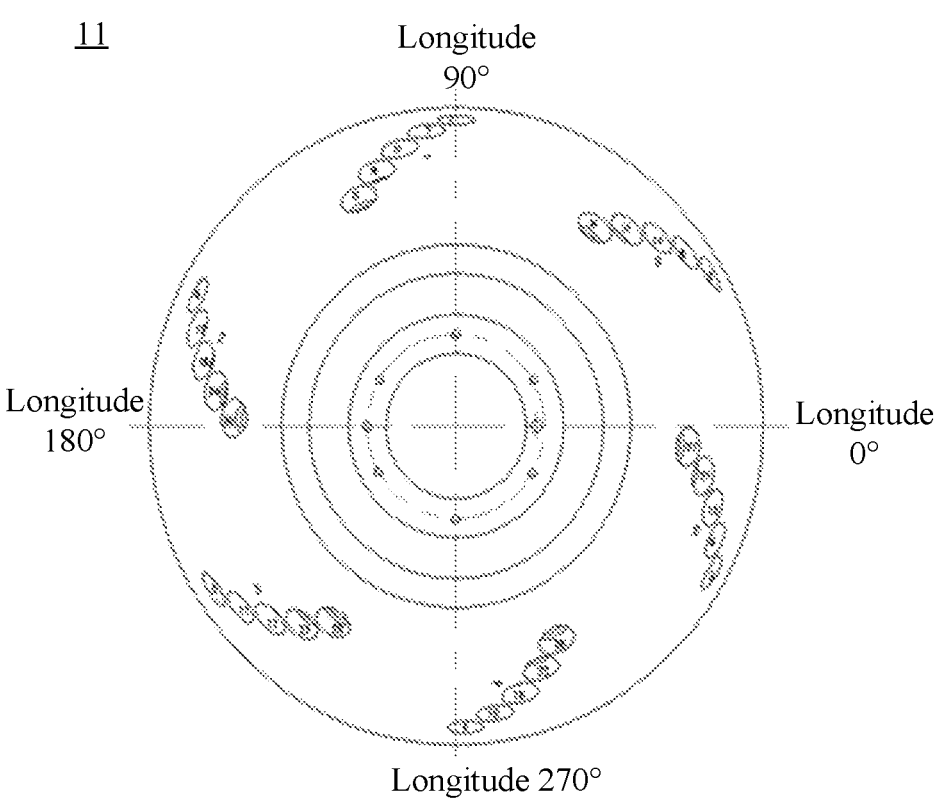
FIG. 3 is a schematic structural top view of a source body in related technologies according to an embodiment of the present disclosure.

The source body 011 of the radiotherapy device in the related technologies is bowl-shaped as shown in FIG. 3. The radioactive sources in the source body 011 may be divided into six groups, wherein each group includes five radioactive sources, i.e., a total of 30 radioactive sources. The collimator 013 is provided with a plurality of collimation channels, and the beams emitted by the radioactive sources intersect at a common focus after passing through the collimation channels. The collimator 013 includes six collimation channel groups. The six collimation channel groups correspond to the positions of the six groups of radioactive sources. Each collimation channel group includes four subgroups. Collimation holes of one subgroup are filled with solid tungsten rods to implement off source shielding. The other subgroups include five collimation holes, and the collimation holes in different subgroups have different sizes.

During treatment, the source body 011 and the collimator 013 may be driven to rotate with respect to each other to switch the collimation holes of different sizes and to implement on/off source by shielding the radioactive sources by the collimator. However, the six groups of collimation holes having different sizes and the on/off source are switched simultaneously, and one of the groups cannot be controlled individually. Therefore, in the course of treatment, radiation of sensitive tissues and organs (such as eyes and other important nerves) is avoided by adjusting a gamma angle, i.e., by adjusting an elevation angle of head.

The present disclosure provides a radiotherapy device. For example, referring to FIG. 9, the radiotherapy device includes a radioactive source apparatus 10. The radioactive source apparatus 10 includes a source body 11 and a collimator 12, the source body 11 is provided with a plurality of radioactive sources 111, an included angle between the plurality of radioactive sources 111 in a longitudinal direction is within a preset included angle range, and beams emitted from the plurality of radioactive sources on the source body 11 intersect at a common focus f after being collimated by the collimator.

Figure 4:
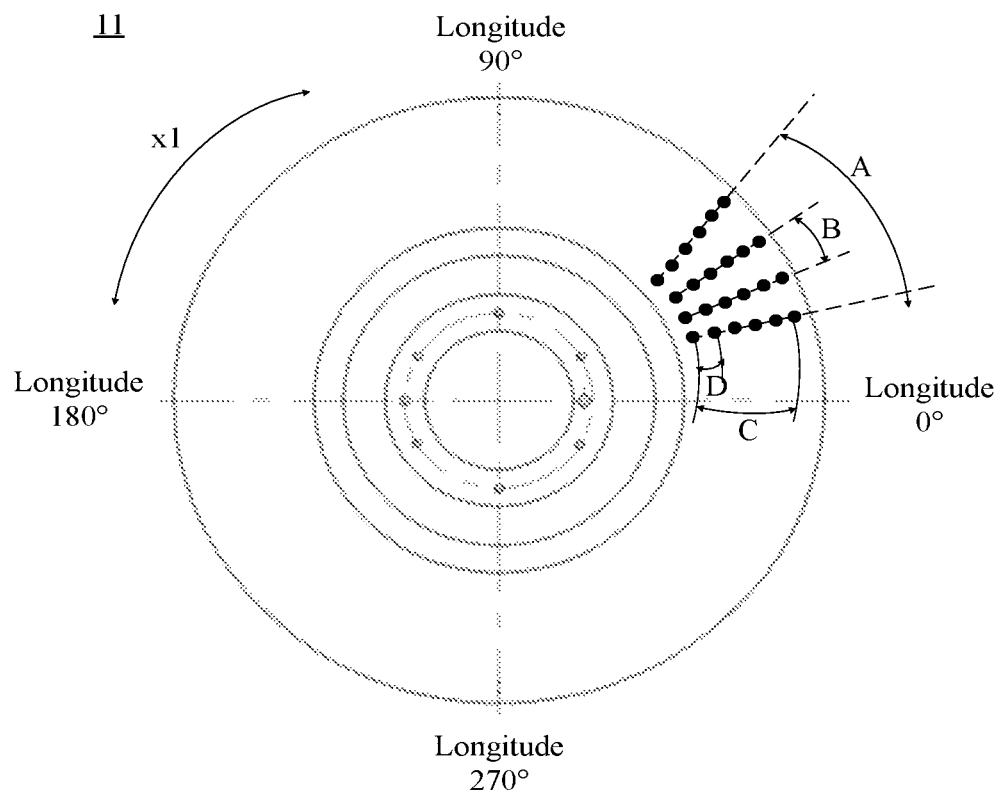
FIG. 4 is a schematic diagram of a source body according to an embodiment of the present disclosure.
Figure 5:
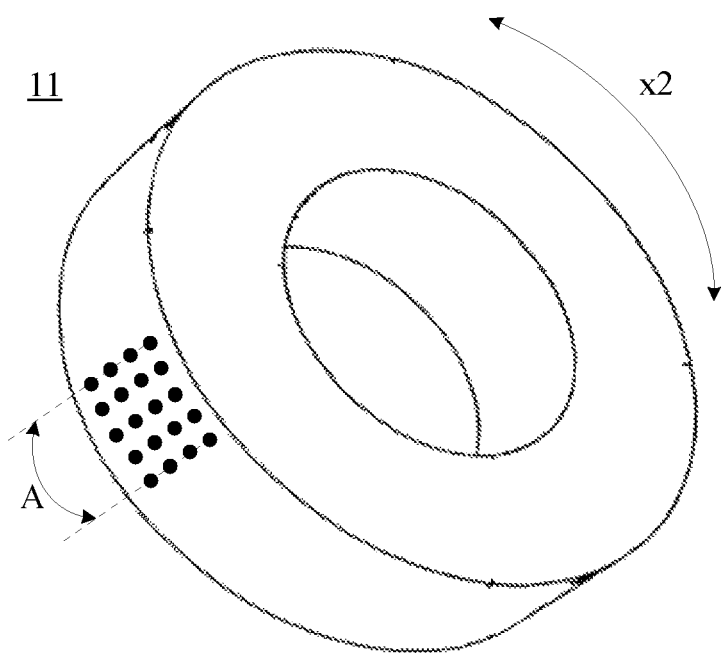
FIG. 5 is a schematic diagram of another source body according to an embodiment of the present disclosure.
Figure 11:
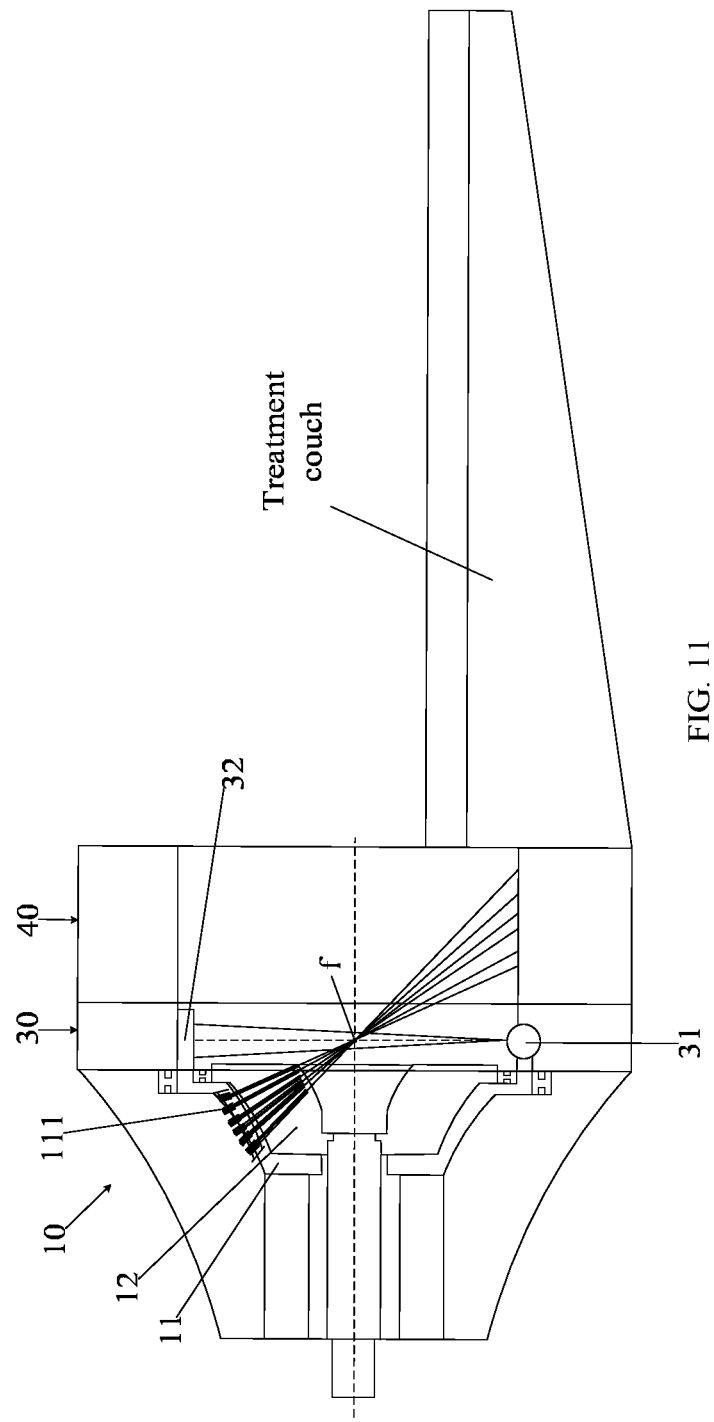
FIG. 11 is a schematic diagram of still another radiotherapy device according to an embodiment of the present disclosure.

For example, as shown in FIG. 4, the source body 11 may be bowl-shaped, and the longitudinal direction of the source body 11 is as shown by Arrow x1 in FIG. 4, which is a direction of longitude 0°-360°. The source body 11 may also be tube-shaped as shown in FIG. 5 (the radiotherapy device is as shown in FIG. 11), and the longitudinal direction of the source body 11 is the direction as shown by Arrow x2 in FIG. 5. Two ends of a round table in FIG. 5 have equal size, or of course, may have different sizes. The present disclosure does not limit the specific shape of the source body, and the longitudinal direction in the present disclosure is described only taking FIG. 4 and FIG. 5 as examples.

In the present disclosure, the included angle between the radioactive sources in the longitudinal direction is within a preset included angle range, and the maximum included angle between the plurality of radioactive sources in the longitudinal direction is within the preset included angle range. Moreover, in the present disclosure, as shown in FIG. 4, the included angle between the radioactive sources in the longitudinal direction is an included angle formed by using centers of the radioactive sources as a reference. It is to be particularly noted here that if the radioactive sources include one row and the centers of the plurality of radioactive sources in the same row are located on the same longitude line, it is believed that the included angle between the plurality of radioactive sources in the longitudinal direction is zero degree. In the present disclosure, the preset included angle range is greater than or equal to zero degree.

Figure 9:
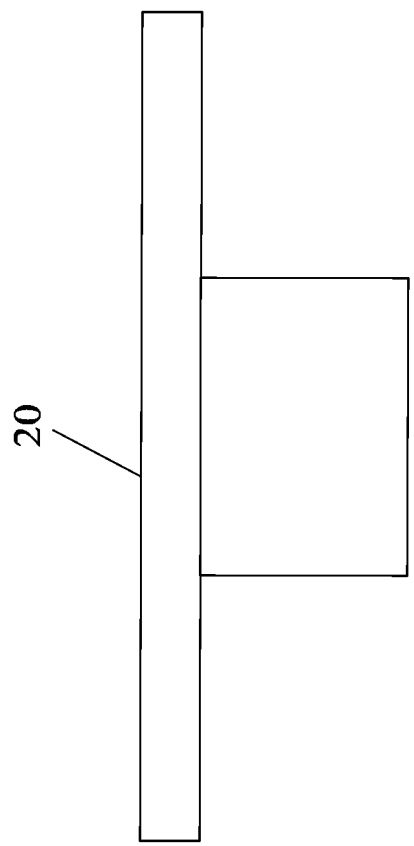
FIG. 9 is a schematic diagram of a radiotherapy device according to an embodiment of the present disclosure.
Figure 9:
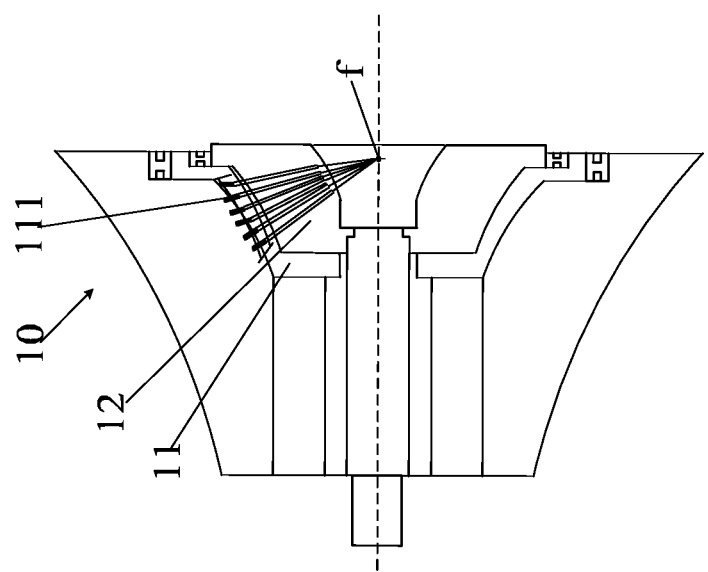
Figure 10:
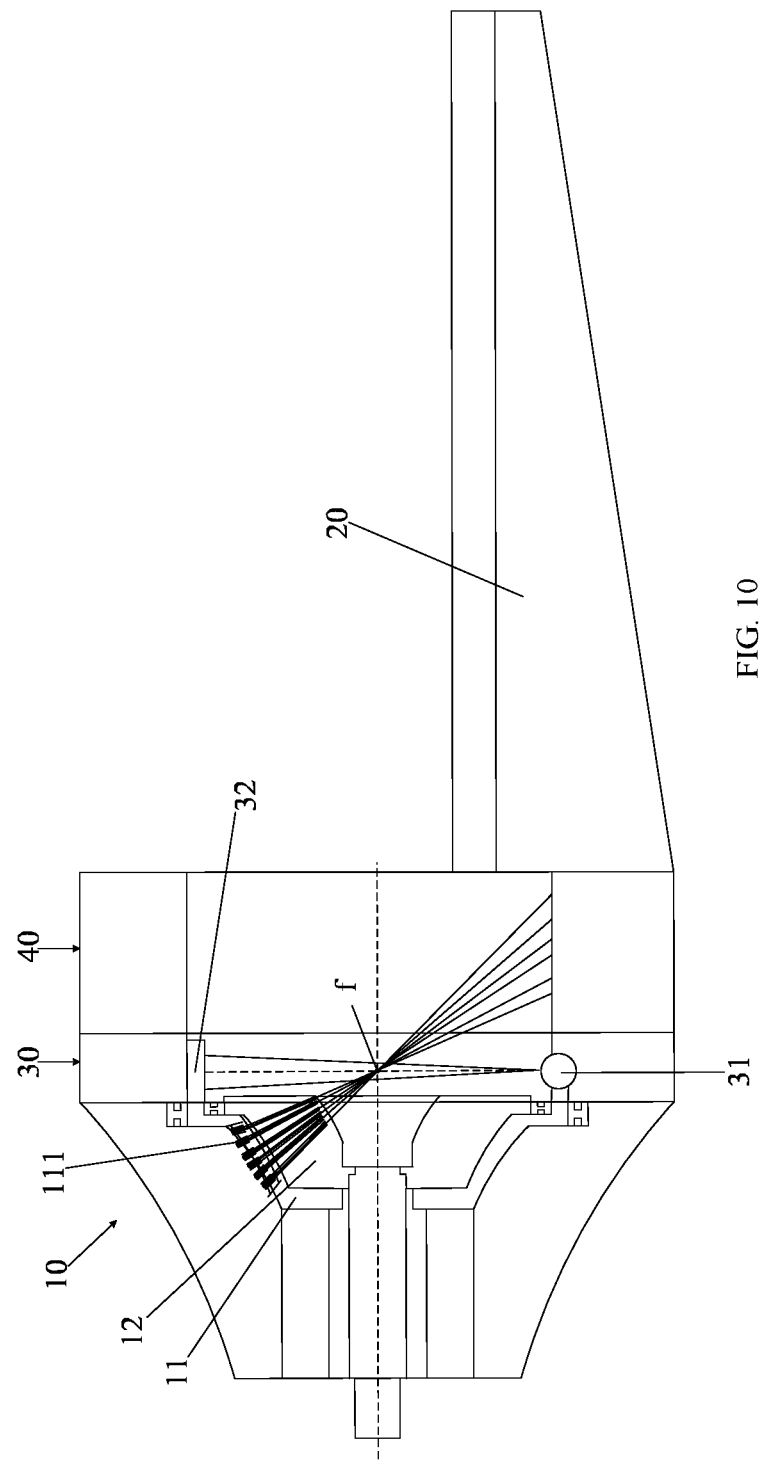
FIG. 10 is a schematic diagram of another radiotherapy device according to an embodiment of the present disclosure.

For example, the radiotherapy device provided by the present disclosure may be as shown in FIG. 9 and FIG. 10, the source body 11 is as shown in FIG. 4, and the included angle between a plurality of radioactive sources 111 in the longitudinal direction is denoted as A. For example, the preset included angle range A may be between 5° and 60°, i.e., 5°≤A≤60°, and the preset included angle range A may be any included angle in the range of from 5° to 60°. For example, the preset included angle range A may be 5°, 8°, 10°, 12°, 18°, 20°, 25°, 30°, 40°, 45°, 50°, or 60°.

A plurality of radioactive sources is arranged on the source body. The number and arrangement of the radioactive sources are not limited in the present disclosure. The number of the radioactive sources may range from 20 to 180, for example, 30 or 180. 24 radioactive sources as shown in FIG. 4 are taken as an example for illustration. The radiotherapy device also includes a collimator. The collimation holes on the collimator correspond to the radioactive sources in number and arrangement, such that the beams emitted from the radioactive sources intersect at a common focus after passing through the collimation holes.

In the radiotherapy device provided by the present disclosure, a plurality of radioactive sources on a source body are distributed within a preset included angle range in a longitudinal direction, and the radioactive sources may be driven by the source body to rotate along a central axis of the radiotherapy device, such that the radioactive sources can be turned off when passing through sensitive tissues or organs, and that the radioactive sources can be turned on when passing through normal tissues and organs. In this way, during the treatment of head tumors, the sensitive tissues and organs such as eyes can be protected from extra damage.

In the radiotherapy device provided by the present disclosure, the radioactive source apparatus 10 further includes a source body driving apparatus configured to drive the source body 11 to rotate about a central axis thereof. The driving apparatus may be a motor, and the radioactive source apparatus 10 may also monitor the driving of the motor to obtain the relative position of the source body 11 in real time so as to determine whether to turn on or off the radioactive sources. The present disclosure does not specifically limit the source body driving apparatus and the position monitoring, and reference may be made to driving technologies in the related technologies, and specific details are omitted herein.

During the treatment, a tumor of a patient may be accurately located at a common focus, such that tumor cells may be killed by radioactive rays. However, if the patient is moved during the treatment, the radioactive rays may deflect, which not only is disadvantageous to the treatment but also is harmful to health of the patient. The common focus of the radiotherapy device in the related technologies is located in a cavity of the radioactive source apparatus, and thus it is impossible to monitor whether the patient's head moves during the treatment. In the radiotherapy device provided by the present disclosure, the common focus is located outside an end surface of the radioactive source apparatus. For example, as shown in FIG. 10 and FIG. 11, the common focus f is located outside the end surface of the radioactive source apparatus, which is advantageous to observe and monitor whether the patient is moved during the treatment.

In the radiotherapy device provided by the present disclosure, for example, the radiotherapy device further includes an imaging apparatus 30. The imaging apparatus 30 is arranged on a side of the radioactive source apparatus 10, and the common focus f is located within an imaging region of the imaging apparatus 30. That is, a tumor of a patient within the imaging region is imaged by the imaging apparatus 30, so to determine whether the patient is moved on the basis of the image. Displacement monitoring based on images has higher accuracy.

For example, the imaging apparatus 30 in the present disclosure may be any combination of one or more of an X-ray imaging apparatus, a CT (Computed Tomography) imaging apparatus, an MR (Magnetic Resonance) imaging apparatus, a DSA (Digital Subtraction Angiography) imaging apparatus, an ultrasound imaging apparatus, or a PET (Positron Emission Computed Tomography) imaging apparatus. For example, the imaging apparatus 30 is the X-ray imaging apparatus. As an example, as shown in FIG. 10, the imaging apparatus 30 may include an X-ray tube 31 and a flat panel detector 32. Alternatively, the imaging apparatus 30 may include two X-ray tubes 31 and two flat panel detectors 32, and beams emitted from the two X-ray tubes 31 intersect. Of course, the imaging apparatus 30 may also be a combination of any two or more different imaging apparatuses. For example, the imaging apparatus may be a combination of the X-ray imaging apparatus and a DSA imaging apparatus. The present disclosure does not limit a specific setup mode of the imaging apparatus, and the above example merely serves as an exemplary description.

Figure 12:
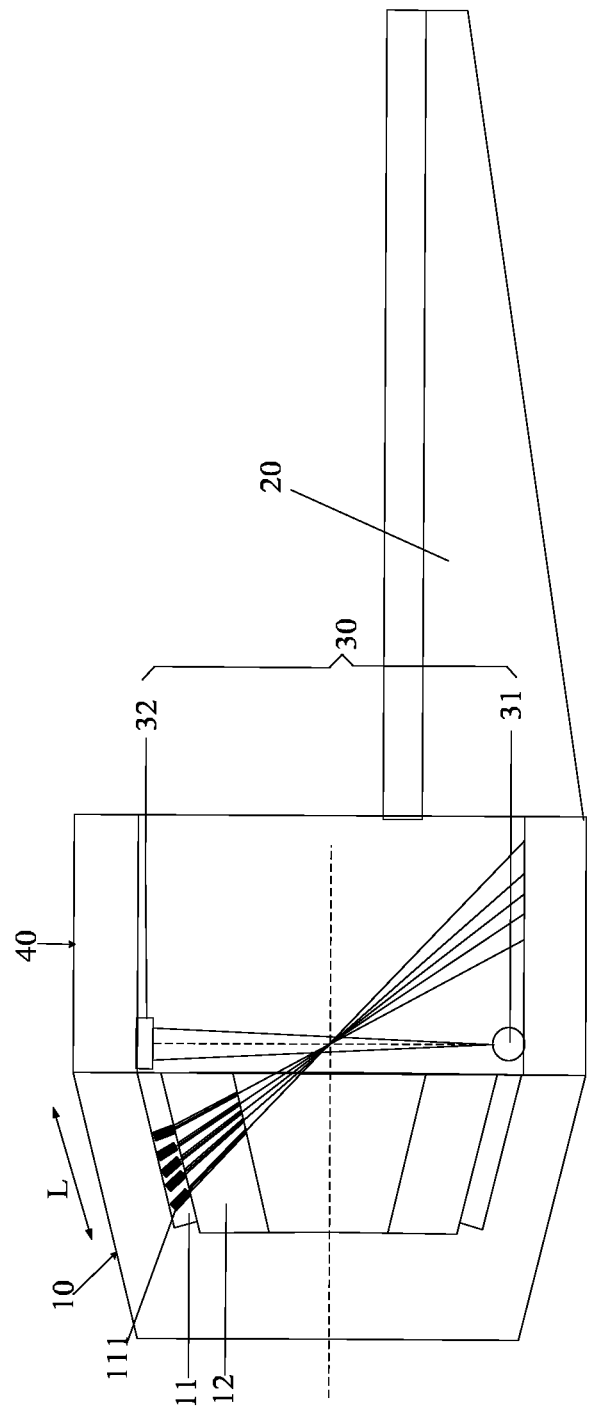
FIG. 12 is a schematic diagram of still another radiotherapy device according to an embodiment of the present disclosure.

In the radiotherapy device as shown in FIG. 11, the source body 11 of the radiotherapy device is tube-shaped, and two ends of the tube-shaped source body 11 have equal diameter. In the radiotherapy device as shown in FIG. 11, the source body 11 and/or the collimator 12 may also move in a direction as shown by the central axis of the radioactive source apparatus 10 to implement on/off source. In the radiotherapy device as shown in FIG. 12, the source body 11 of the radiotherapy device is tube-shaped, and two ends of the tube-shaped source body 11 have different diameters. In the radiotherapy device as shown in FIG. 12, the source body 11 and/or the collimator 12 may also move in the direction L to implement on/off source. Of course, on/off source may be implemented through rotation, which is not limited in the present disclosure.

As shown in FIG. 10, the imaging apparatus 30 may be a bulb tube 31 and a flat panel detector 32 separately provided with a fixing device to fix the imaging apparatus 30, or the imaging apparatus 30 may also be separately provided with a driving apparatus to drive the bulb tube 31 and the flat panel detector 32 to rotate. Alternatively, as shown in FIG. 11, the imaging apparatus 30 may be fixedly arranged in a shielding apparatus 40, the specific position and structure of the shielding apparatus are not limited in the present disclosure, and the above example merely serves as an exemplary description.

In addition, the radiotherapy device further includes a treatment couch 20 for carrying a patient. As shown in FIG. 9-FIG. 12, the present disclosure does not limit the specific structure or movement form of the treatment couch 20, which may be a three-dimensional couch as shown in FIG. 10-FIG. 12, or may be a six-dimensional couch as shown in FIG. 10. The treatment couch 20 may be selectively configured according to treatment needs, and related details are omitted herein.

In the radiotherapy device provided by the present disclosure, there is further provided with an anti-sinking component between the collimator and the source body. Referring to FIG. 9 to FIG. 10, the anti-sinking component is a bearing.

In the radiotherapy device provided by the present disclosure, the radioactive source apparatus further includes a shielding apparatus 40. The shielding apparatus 40 is located on a side of the radioactive source apparatus 10. Beams emitted from the radioactive source 111 are shielded by the shielding apparatus 40 after passing through the common focus f. For example, as shown in FIG. 10-FIG. 12, the shielding apparatus 40 is located at a side of the common focus f of the radioactive source apparatus 10, and the beams emitted from the radioactive source 111 are shielded by the shielding apparatus 40 after passing through the common focus f, so as to avoid excessive radiation in a treatment room. For example, if the shielding apparatus 40 is shaped like an annular body, all the rays from the radioactive source 111 rotating about the central axis are received by the shielding apparatus 40. Alternatively, the shielding apparatus 40 is a shielding block that can rotate along the central axis of the radioactive source apparatus 10 to follow the radioactive source 111 to rotate so as to receive the rays having passed through the common focus f. It is to be noted that when the treatment couch 20 carries the patient to move, the shielding apparatus 40 is provided with a channel to facilitate the movement of the treatment couch 40.

The source body in the present disclosure is specifically introduced and described below.

The present disclosure provides a source body, wherein the source body 11 is provided with a plurality of radioactive sources 111, and an angle between the plurality of radioactive sources 111 in a longitudinal direction is within a preset angle range. For example, as shown in FIG. 4, the angle between the plurality of radioactive sources in the longitudinal direction is within a preset angle range A. For example, the preset angle range A may be between 5° and 60°, i.e., 5°≤A≤60°, and the preset angle range A may be any angle in the range of from 5° to 60°. For example, the preset angle range A may be 5°, 8°, 10°, 12°, 18°, 20°, 25°, 30°, 40°, 45°, 50°, or 60°. The number and arrangement of the radioactive sources are not limited in the present disclosure. The number of the radioactive sources generally may range from 20 to 180, for example, 30 or 180. 24 radioactive sources as shown in FIG. 4 are taken as an example for illustration.

For example, in the source body provided by the present disclosure, in the longitudinal direction, the plurality of radioactive sources are classified into a plurality of groups, and the included angle between two adjacent groups of radioactive sources ranges from 2° to 15°. For example, among the plurality of groups of radioactive sources, the included angle between any two adjacent groups of radioactive sources are the same, or the included angles between two adjacent different groups of radioactive sources are different, which is not limited in the present disclosure, and the above example as shown in FIG. 4 merely serves as an exemplary description. As shown in FIG. 4, the plurality of radioactive sources are divided into four rows, taking an example where the included angle between adjacent rows of collimation holes is denoted as B (in FIG. 4, two rows are taken as an example), the included angle B may range from 2° to 15°, i.e., 2°≤B≤15°, and the preset included angle B may be any included angle in the range of from 2° to 15°. For example, the preset included angle range B may be 2°, 2.5°, 3°, 5°, 6°, 8°, 10°, 12°, or 15°.

In the source body provided by the present disclosure, the included angle between the plurality of radioactive sources in a latitudinal direction ranges from 20° to 60°. For example, as shown in FIG. 4, a plurality of radioactive sources are provided within a preset range C of the source body 11 in the longitudinal direction. For example, the preset included angle range C may be between 20° to 60°, i.e., 20°≤C≤60°, and the preset included angle range C may be any included angle in the range of from 20° to 60°. For example, the preset included angle range C may be 20°, 25°, 30°, 38°, 40°, 45°, 50°, 53°, or 60°.

For example, in the source body provided by the present disclosure, in the latitudinal direction, the included angle between any two adjacent radioactive sources ranges from 1° to 10°. For example, among the plurality of groups of radioactive sources, the included angle between any two adjacent groups of radioactive sources are the same, or the included angles between any two adjacent groups of radioactive sources are different, which is not limited in the present disclosure, and the above example as shown in FIG. 4 merely serves as an exemplary description. For example, as shown in FIG. 4, taking two radioactive sources as an example, an included angle between the two radioactive sources in the latitudinal direction is denoted as D, the included angle D may range from 1° to 10°, i.e., 1°≤D≤10°, and the preset included angle D may be any included angle in the range of from 1° to 10°. For example, the preset included angle D may be 1°, 2°, 3°, 5°, 6°, 8°, 9°, or 10°.

For the source body 11 as shown in FIG. 4, an example is taken where the radioactive sources are classified into a plurality of rows in the longitudinal direction and the radioactive sources in the same row have the same longitude, and the radioactive sources are classified into a plurality of rows in the latitudinal direction and the radioactive sources in the same row have the same latitude. Further, to implement non-coplanar radiation and to better protect normal tissues, in the source body provided by the present disclosure, the plurality of radioactive sources has different positions in the latitudinal direction. That is, each radioactive source has different latitudes.

Figure 6:
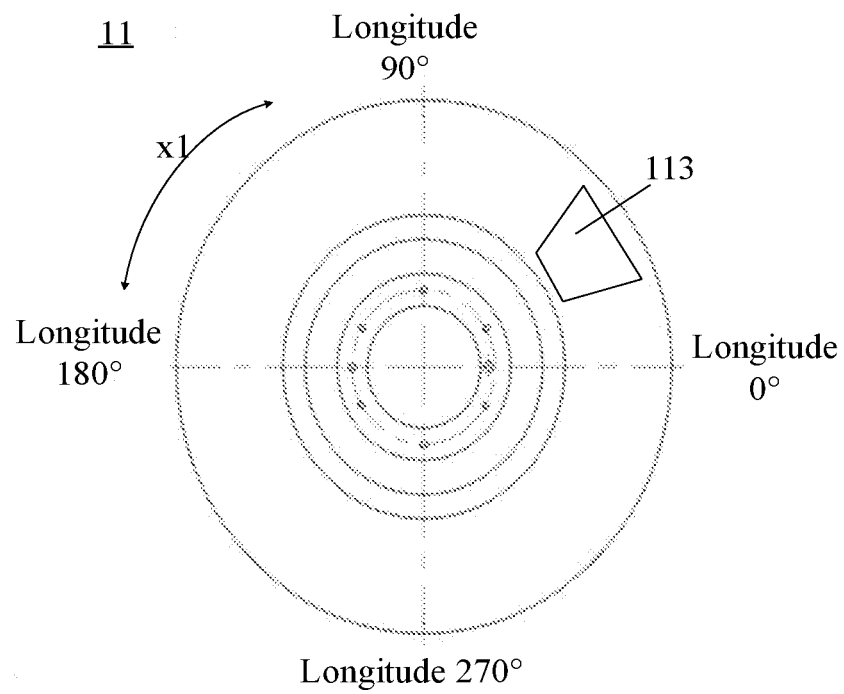
FIG. 6 is a schematic diagram of still another source body according to an embodiment of the present disclosure.
Figure 7:
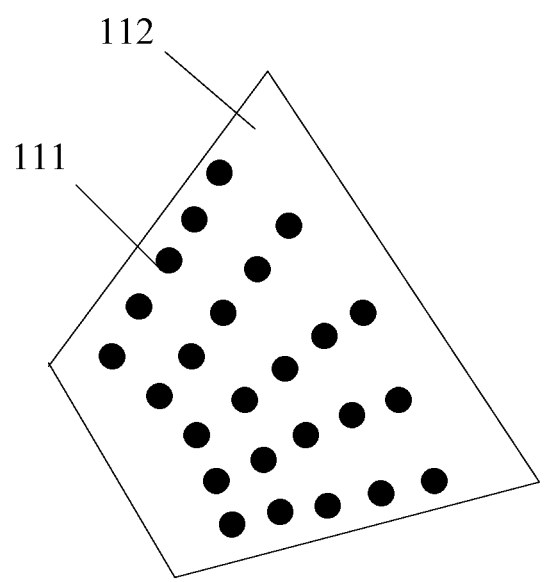
FIG. 7 is a schematic diagram of a source case according to an embodiment of the present disclosure.

The source body provided by the present disclosure is provided with a plurality of radioactive source holes, and the radioactive sources are fixedly mounted in the radioactive source holes. Alternatively, the source body is provided with a source case position matching a shape of a source case, the source case may be fixedly mounted on the source case position, and the source case is provided with a plurality of radioactive sources. For example, as shown in FIG. 6 and FIG. 7, a plurality of radioactive sources 111 are arranged on the source case 112, and a source case position 113 is arranged on the source body 11. The source case position 113 is internally provided with the source case 112, wherein the source case position 113 may be a through hole or a blind hole, and a plurality of collimation holes are arranged on the source body 11, such that beams from the radioactive source 111 may be emitted through the collimation holes. The present disclosure does not limit shapes or structures of the source case and the source case position, and the above examples as shown in FIG. 6 to FIG. 7 merely serve as an exemplary description.

The source body is further provided with a source case connection portion configured to fix the source case located at the source case position. Similarly, the source case is also provided with a connection portion configured to connect the source case. For example, the source body and the source case may be connected by screws or by snaps. The connection and fixation between the source case and the source case position are not limited in the present disclosure, and the above examples merely serve as an exemplary description.

In the source body provided by the present disclosure, the source case is further provided with a connection portion configured to replace the source case. For example, the connection portion of the source case may be a screw hole, which may be in threaded connection with a source guide rod. Alternatively, the connection portion of the source case may be connected by magnet attraction to the source guide rod. The connection between the source case and the source guide rod and the replacement of the source case are not limited in the present disclosure, and the above example merely serves as an exemplary description.

In the source body provided by the present disclosure, the source case and the source body are formed of different materials. For example, the source case may be formed of tungsten alloy, and the source body may be formed of cast iron.

The source body 11 provided by the present disclosure is bowl-shaped, or generally is also referred to as pan-shaped, helmet-shaped, or hemisphere-shaped, as shown in FIG. 4. Alternatively, the source body 11 may be tube-shaped, as shown in FIG. 5, and diameters of two ends of the tube-shaped source body 11 may be equal or unequal. In FIG. 5, an example is taken where the diameters of the two ends are equal. Alternatively, the source body also may be sheet-shaped. The present disclosure does not specifically limit the specific structure and shape of the source body, and the above example merely serves as an exemplary description.

In the source body provided by the present disclosure, beams emitted from a plurality of radioactive sources intersect at a common focus after being collimated, and the common focus is located on the central axis of the source body, so as to facilitate accurate positioning of the radiotherapy device. The source body may be fixed, or the source body may be driven by a rotary apparatus to rotate about a central axis in a 360° circle or to rotate to and fro.

Figure 8:
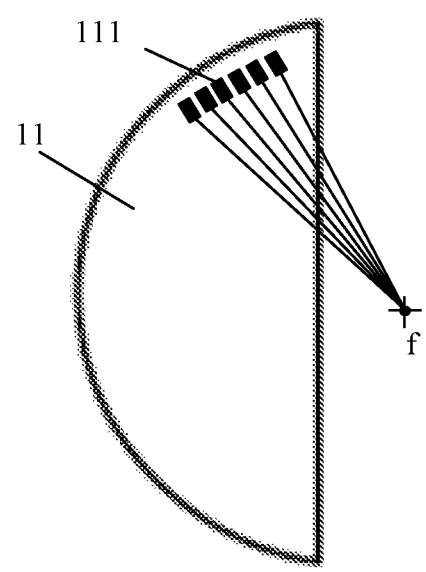
FIG. 8 is a schematic structural diagram of a common focus located outside an end surface of the source body according to an embodiment of the present disclosure.

In the source body provided by the present disclosure, the common focus is located outside an end surface of the source body. For example, as shown in FIG. 8, the common focus f is located outside the end surface of the source body 11. The source body 11 is arranged in the entire radiotherapy device, as shown in FIG. 10-FIG. 12, the common focus f is located outside the end surface of the radioactive source apparatus, to facilitate monitoring of a patient or tumor movement.

Figure 13:
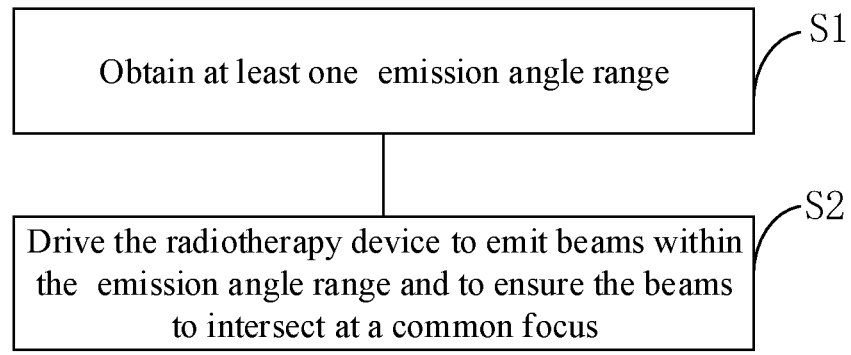
FIG. 13 is a schematic diagram of a control driving method according to an embodiment of the present disclosure.

The present disclosure provides a control driving method for a radiotherapy device. The radiotherapy device is the radiotherapy device provided by the present disclosure. For example, the radiotherapy device may be the radiotherapy device as shown in FIG. 9 to FIG. 11. As shown in FIG. 13, this control driving method includes:

Step S1: obtaining at least one beam emission angle range; and

Step S2: driving the radiotherapy device to emit beams within the beam emission angle range and to ensure the beams to intersect at a common focus.

Figure 14:
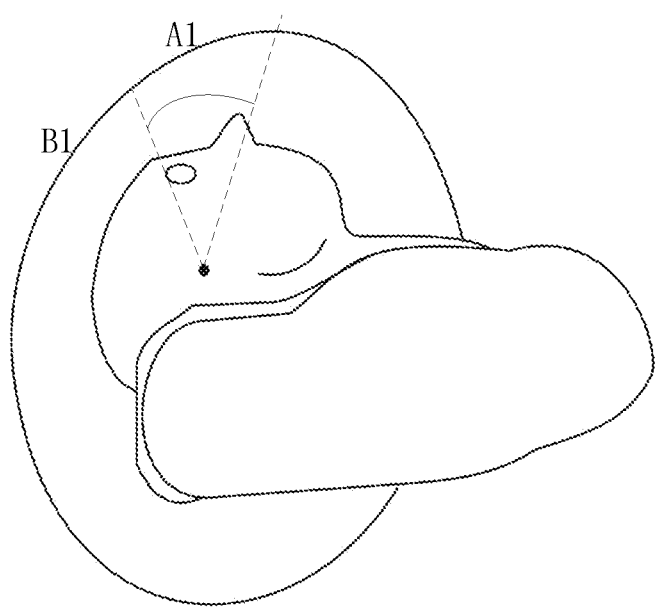
FIG. 14 is a schematic diagram of a radiation treatment according to an embodiment of the present disclosure.
Figure 15:
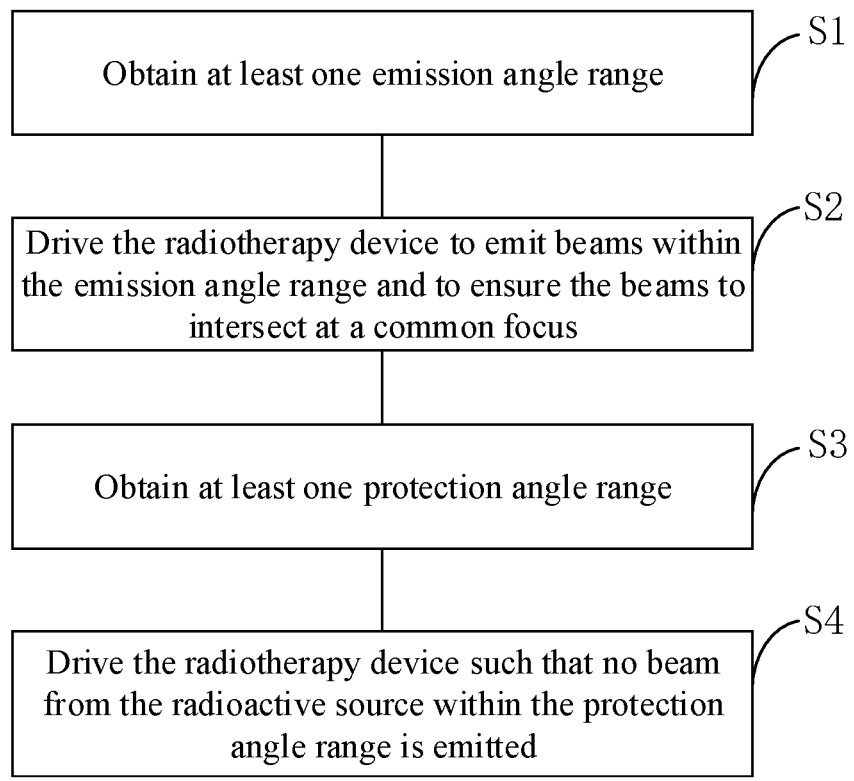
FIG. 15 is a schematic diagram of another control driving method according to an embodiment of the present disclosure.

It is to be noted that a preset zero position is generally set for the driving apparatus in the radiotherapy device, and the zero position serves as a reference during the radiation treatment to determine to drive within a drive angle range. In the present disclosure, the beam emission angle range may be an angle range required for the radiotherapy device to emit beams for radiation treatment, wherein the angle range is included in a corresponding treatment plan worked out by a physician according to a tumor image of a patient, and the angle range is an angle range for the driving apparatus to drive. For example, as shown in FIG. 14, in the corresponding treatment plan worked out by the physician according to the tumor image of the patient, the radiotherapy device performs a radiation treatment in a B1 interval, but does not perform the radiation treatment in an A1 interval (an A1 region includes radiation regions of two eyes to prevent rays from causing damage to optic nerves). The beam emission angle range is a drive angle range where the driving apparatus drives the radioactive source to radiate in the B1 interval, and a protection angle range is a drive angle range where the driving apparatus drives the radioactive source not to radiate in the A1 interval. During the radiation treatment, it is only necessary to perform rotatory radiation within the drive angle range of the radiation in the B1 interval, such that sensitive tissues such as the eyes may be prevented from damaging. For example, the drive angle range is a rotation angle of the motor. In the present disclosure, if the radiotherapy device rotates more than 360°, the drive angle range also exceeds 360°. Alternatively, if the radiotherapy device rotates more than 360°, the number of rotations and the drive angle range corresponding to different numbers of rotations are demarcated.

Of course, during the radiation treatment, rotatory radiation may also be performed on the A1 region and the B1 region. In this case, the beam emission angle range is the drive angle range for radiation in the A1 interval and the B1 region. For example, the beam emission angle range may be 360°. At this moment, dosage received by the sensitive tissues such as the optic nerves may be reduced by reducing radiation time to protect the sensitive tissues and organs.

According to a control driving method provided by the present disclosure, a radiotherapy device includes a plurality of radioactive sources, and source points of the plurality of radioactive sources are within a preset angle range in a longitudinal direction. The control driving method includes: obtaining at least one beam emission angle range; and driving the radiotherapy device to emit beams within the beam emission angle range and to ensure the beams to intersect at a common focus, such that sensitive tissues and organs such as eyes can be protected from extra damage during the treatment of head tumors.

As shown in FIG. 5, the control driving method provided by the present disclosure further includes:

Step S3: obtaining at least one protection angle range. The at least one protection angle range is less than 360°.

Figure 16:
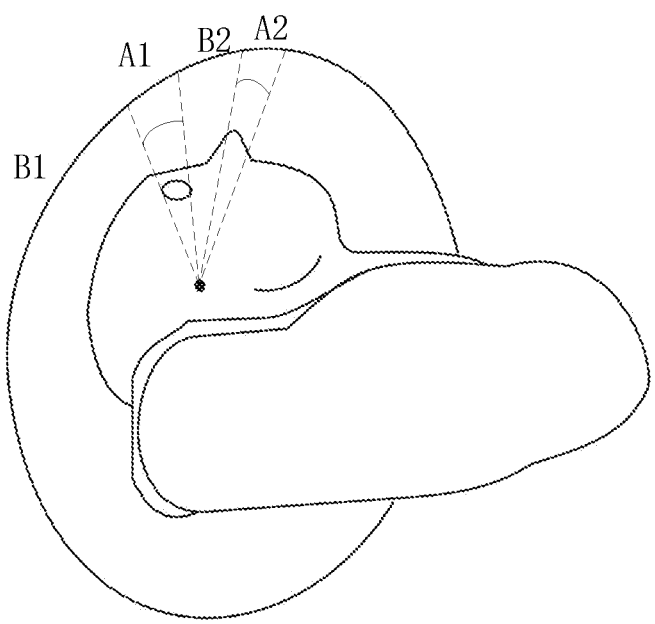
FIG. 16 is a schematic diagram of another radiation treatment according to an embodiment of the present disclosure.

As shown in FIG. 16, the radiotherapy device performs a radiation treatment in a B1 interval and a B2 interval, but does not perform the radiation treatment in an A1 interval and an A2 interval (the A1 interval and the A2 interval correspond to eye regions to prevent rays from causing damage to optic nerves). The beam emission angle range is a drive angle range where the driving apparatus drives the radioactive source to radiate in the B1 interval and the B2 interval, and the protection angle range is a drive angle range where the driving apparatus drives the radioactive source not to radiate in the A1 interval or the A2 interval.

Step S4: driving the radiotherapy device such that no beam from the radioactive source within the protection angle range is emitted.

According to a control driving method provided by the present disclosure, a radiotherapy device includes a plurality of radioactive sources, and source points of the plurality of radioactive sources are within a preset angle range in a longitudinal direction. The control driving method includes: obtaining at least one beam emission angle range and at least one protection angle range; and driving the radiotherapy device to emit beams within the beam emission angle range and to ensure the beams to intersect at a common focus, such that no beam from the radioactive sources within the protection angle range is emitted. In this way, during the treatment of head tumors, the sensitive tissues and organs such as eyes can be protected from extra damage.

For example, in an embodiment provided by the present disclosure, the radiotherapy device is configured to operate at first speeds within the at least one protection angle range; and the radiotherapy device is configured to operate at second speeds within the at least one emission angle range.

For example, according to different treatment plans worked out for different patients, the first speeds are different from the second speeds. Of course, according to different treatment plans worked out for different patients, the first speeds can be the same as the second speeds.

For example, in an embodiment provided by the present disclosure, the at least one protection angle range and the at least one emission angle range are less than 360°.

For example, the radiotherapy device is driven to reciprocate within the preset angle range, and the preset angle range is less than 360°. For example, the preset angle range can be 270°, and the radiotherapy device rotates to and fro in the preset angle range. Of course, according to different clinical needs, the preset angle range can be 260°, 240° and the like. The preset angle range is not limited in the present disclosure, and the above examples merely serve as an exemplary description.

For example, the preset angle range may comprise the at least one protection angle range and the at least one emission angle range. For example, the preset angle range comprises one protection angle range and one emission angle range. Alternatively, the preset angle range comprises two protection angle ranges and one emission angle range. Alternatively, the preset angle range may comprise more than two protection angle ranges and more than two emission ranges.

For example, the at least one beam emission angle range is adjacent to the at least one protection angle range. As shown in FIG. 16, a radiation treatment is performed in the B1 interval and the B2 interval, but the radiation treatment is neither performed in the A1 interval nor performed in the A2 interval. Because the B1 interval is adjacent to the A1 interval, the beam emission angle range corresponding to the B1 interval is adjacent to the protection angle range corresponding to the A1 interval.

According to the control driving method provided by the present disclosure, the number of the beam emission angle ranges is at least two, and the radiotherapy device has different speeds within the at least two beam emission angle ranges. For example, referring to FIG. 16, when the radiation treatment is performed in the B1 interval and the B2 interval, the beam emission angle range corresponding to the B1 interval and the beam emission angle range corresponding to the B2 interval are obtained. The speed of the radiotherapy device within the beam emission angle range corresponding to the B1 interval is denoted as V1, and the speed of the radiotherapy device within the beam emission angle range corresponding to the B2 interval is denoted as V2, V1≠V2. Radiation time at different positions may be adjusted by adjusting the speed, such that dosage of the focus is adjusted.

For example, as shown in FIG. 14, when a rotatory radiation is performed in the A1 region and the B1 region during the radiation treatment, the beam emission angle range is the drive angle range for radiation performed in the A1 region and the B1 region. The speed of the radiotherapy device within the beam emission angle range corresponding to the B1 interval is denoted as V1, and the speed of the radiotherapy device within the beam emission angle range corresponding to the A1 interval is denoted as V2, V1<V2. That is, the speed in the A1 interval is greater than the speed in the B1 interval, such that the dosage received by sensitive tissues in the A1 interval is reduced to protect the sensitive tissues and organs.

It is to be noted that the drive angle range in the present disclosure is the rotation angle of the motor, and the drive angle range also exceeds 360°. For example, if the rotation angle of the motor exceeds 360°, the number of rotations and the drive angle range corresponding to different numbers of rotations are demarcated. The radiotherapy device has different speeds within at least two beam emission angle ranges, and has different drive speeds in the same radiation interval corresponding to different numbers of rotations. For example, if planned treatment time for a radiation treatment is 2 min, and 1 min is required for per rotation of the motor, as shown in FIG. 16, the drive speed for radiation in the B1 region within the beam emission angle range of the first rotation is denoted as V1, and the drive speed for radiation in the B1 region within the beam emission angle range of the second rotation is denoted as V2, V1≠V2.

According to the control driving method provided by the present disclosure, for example, as shown in above figures, two beam emission angle ranges having different speeds are adjacent to each other.

According to the control driving method provided by the present disclosure, the radiotherapy device is driven to reciprocate within the beam emission angle range. For example, if only one beam emission angle range is obtained, the radiotherapy device may reciprocate within the beam emission angle range to increase the dosage received by a tumor. Of course, if a plurality of beam emission angle ranges is obtained, the radiotherapy device may also reciprocate within the beam emission angle range to increase the dosage received by the tumor.

For example, the at least one protection angle range is determined according to the image of the patient.

For example, the at least one emission angle range is determined according to the image of the patient.

For example, wherein the radiotherapy device further comprises an imaging apparatus, the method further comprises: controlling the imaging apparatus to obtain the image of the patient.

Figure 17:
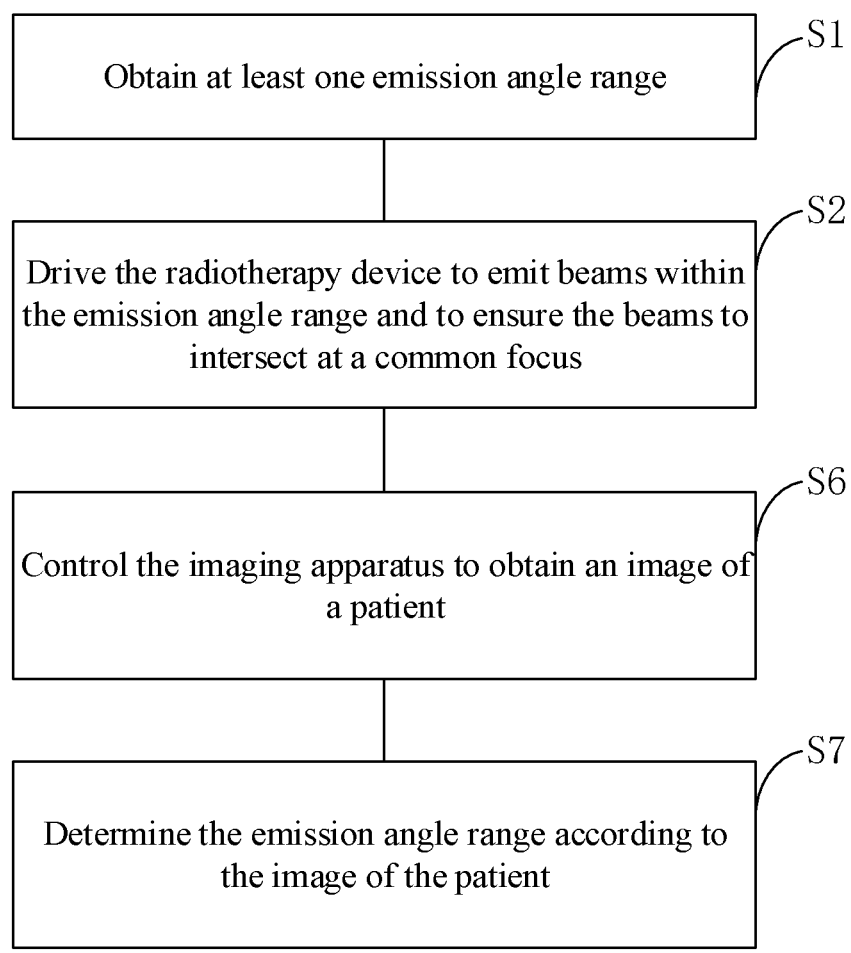
FIG. 17 is a schematic diagram of another control driving method according to an embodiment of the present disclosure.

For example, in the radiotherapy device as shown in FIG. 10-FIG. 12, the common focus is located outside an end surface of the radioactive source apparatus. The radiotherapy device further includes an imaging apparatus, and the common focus is located within an imaging region of the imaging apparatus. As shown in FIG. 17, the control driving method also includes:

Step S6: controlling the imaging apparatus to obtain an image of a patient.

Step S7: determining the beam emission angle range according to the image of the patient.

It is to be noted that the beam emission angle range in Step S1 may be a beam emission angle range determined by a physician based on the image of the patient before the radiation treatment, and during the treatment, the beam emission angle range may be determined or adjusted based on the obtained image.

Figure 18:
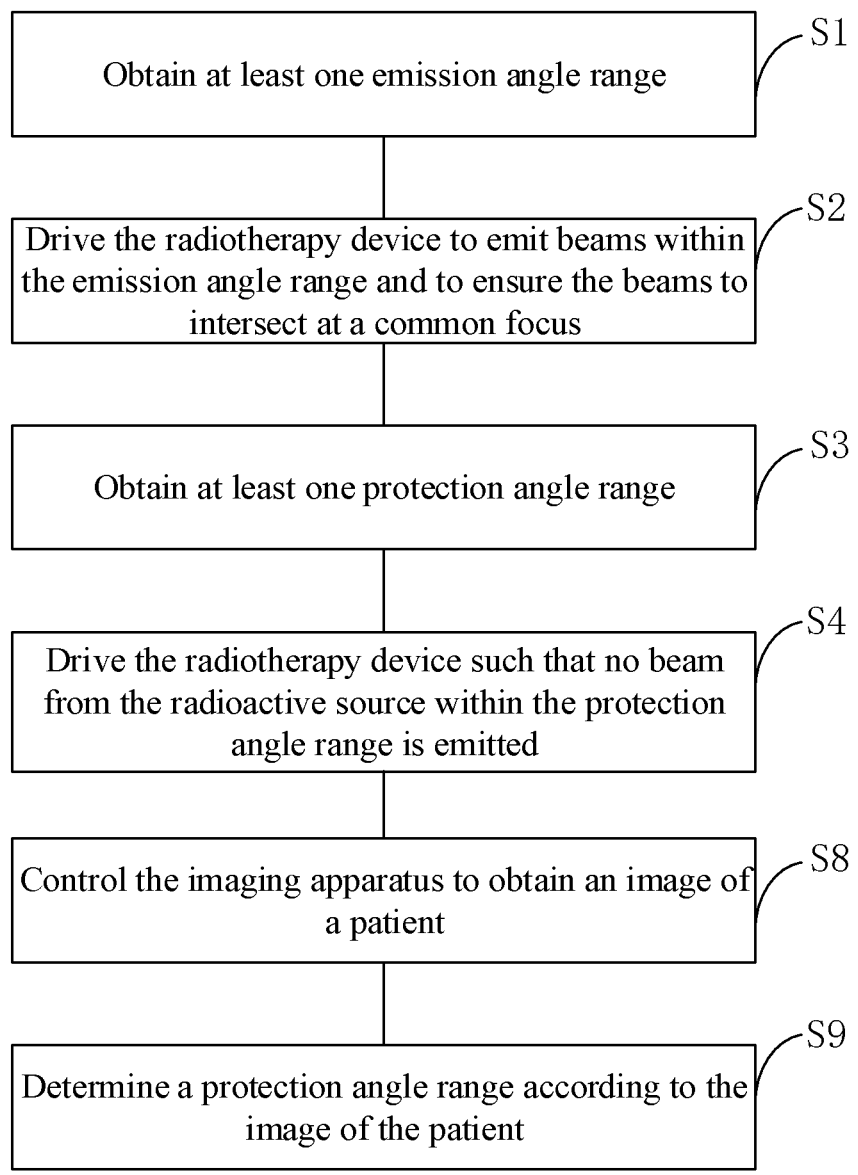
FIG. 18 is a schematic diagram of still another control driving method according to an embodiment of the present disclosure.

For example, the radiotherapy device as shown in FIG. 10-FIG. 12 further includes an imaging apparatus, and the common focus is located within an imaging region of the imaging apparatus. As shown in FIG. 18, the control driving method also includes:

Step S8: controlling the imaging apparatus to obtain an image of a patient; and

Step S9: determining a protection angle range according to the image of the patient.

Similarly, the protection angle range in Step S3 may be a protection angle range determined by the physician based on the image of the patient before the radiation treatment, and during the treatment, the protection angle range may be determined or adjusted based on the obtained image.

The embodiments described above are merely alternative embodiments of the present disclosure, and are not intended to limit the present disclosure. All modifications, equivalent substitutions and improvements made within the spirit and principle of the present disclosure shall fall within the protection scope of the present disclosure.

What is claimed is:

1. A control driving method for a radiotherapy device, the radiotherapy device comprising a collimator and a plurality of radioactive sources, wherein the radioactive sources are disposed within a preset angle range in a longitude direction, the longitude direction being a circular direction perpendicular to a central axis of the radiotherapy device, and the radioactive sources are configured to emit beams that intersect at a common focus after being collimated by the collimator, the method comprising:
   obtaining at least one protection angle range;
   driving the radiotherapy device such that no beam from the plurality of the radioactive sources within the at least one protection angle range is emitted;
   obtaining at least two emission angle ranges of the emitted beams; and
   driving the radiotherapy device to emit the beams within the at least two emission angle ranges to ensure the beams intersect at the common focus.

2. The control driving method according to claim 1, wherein the radiotherapy device is configured to operate at first speeds within the at least one protection angle range; and
   the radiotherapy device is configured to operate at second speeds within the at least two emission angle ranges.

3. The control driving method according to claim 1, wherein the at least one protection angle range and the at least two emission angle ranges are less than 360°.

4. The control driving method according to claim 1, wherein the radiotherapy device is driven to reciprocate within the preset angle range, and the preset angle range is less than 360°.

5. The control driving method according to claim 4, wherein the preset angle range comprises the at least one protection angle range and the at least two emission angle ranges.

6. The control driving method according to claim 1, wherein the at least one protection angle range is determined according to an image of a patient.

7. The control driving method according to claim 6, wherein the radiotherapy device further comprises an imaging apparatus, the method further comprising:
controlling the imaging apparatus to obtain the image of the patient.

8. The control driving method according to claim 1, wherein the at least two emission angle ranges are determined according to an image of a patient.

9. The control driving method according to claim 8, wherein the radiotherapy device further comprises an imaging apparatus, the method further comprising:
controlling the imaging apparatus to obtain the image of the patient.

10. The control driving method according to claim 1, wherein the at least two emission angle ranges are adjacent to the at least one protection angle range.

11. The control driving method according to claim 1, wherein the preset angle range is between 5° to 60°.

12. The control driving method according to claim 1, wherein the radioactive sources are divided into a plurality of groups in the longitude direction, and an angle between two adjacent groups of the radioactive sources ranges from 2° to 15°.

13. The control driving method according to claim 1, wherein the radioactive sources are arranged on and an angle between the radioactive sources in a latitude direction ranges from 20° to 60°, the latitude direction being parallel with a central axis of the source body.

14. The control driving method according to claim 1, wherein the radioactive sources are arranged on a source body, and an angle between any two adjacent radioactive sources in a latitude direction ranges from 1° to 10°, the latitude direction being parallel with a central axis of the source body.

15. The control driving method according to claim 1, wherein the radioactive sources have different positions in a latitude direction, the latitude direction being parallel with a central axis of a source body on which the radioactive sources are arranged.

16. The control driving method according to claim 1, wherein the radioactive sources are arranged on a source body, the source body is provided with a plurality of radioactive source holes, and the radioactive sources are fixedly mounted in the radioactive source holes; or
the source body is provided with a source case position fitting a shape of a source case, the source case is fixedly mounted on the source case position, and the source case is provided with the radioactive sources.

17. The control driving method according to claim 1, wherein the radioactive sources are arranged on a source body, and the source body is bowl-shaped, tube-shaped, or sheet-shaped.

18. The control driving method according to claim 1, wherein the radioactive sources are arranged on a source body, and the source body is configured to rotate about a central axis of the source body in a 360° circle or is configured to rotate to and fro.

* * * * *